| United States Patent [19] | [11] Patent Number: 4,961,774 |
| --- | --- |
| Brochier | [45] Date of Patent: Oct. 9, 1990 |

[54] PROCESS FOR THE CULTIVATION OF AQUATIC PLANTS, THE RESULTING PLANTS, AND THEIR USES

[75] Inventor: José Brochier, Castries, France

[73] Assignee: Spie Batignolles, Puteaux, France

[21] Appl. No.: 153,718

[22] Filed: Feb. 8, 1988

Related U.S. Application Data

[62] Division of Ser. No. 908,817, Sep. 18, 1986, abandoned.

[30] Foreign Application Priority Data

Sep. 23, 1985 [FR] France .................... 85 14055

[51] Int. Cl.$^5$ ............................................ A01N 65/00
[52] U.S. Cl. ........................................ 71/77; 71/79; 424/195.1
[58] Field of Search ............... 71/77, 79; 424/195.1; 47/59, 62

[56] References Cited

U.S. PATENT DOCUMENTS

| 2,949,700 | 8/1960 | Kathrein | 435/67 |
| 3,402,506 | 9/1968 | Renfro | 47/59 |
| 4,169,716 | 10/1979 | Ashmead | 71/77 |
| 4,169,717 | 10/1979 | Ashmead | 71/77 |
| 4,251,508 | 2/1981 | Monsod, Jr. | 424/195.1 |
| 4,251,508 | 2/1981 | Monsod, Jr. | 424/195.1 |
| 4,297,130 | 10/1981 | Moore, Jr. | 71/119 |
| 4,404,015 | 9/1983 | Menon et al. | 71/77 |

FOREIGN PATENT DOCUMENTS 2559639 2/1984 France .
2032746 5/1980 United Kingdom .

*Primary Examiner*—Glennon H. Hollrah
*Assistant Examiner*—Amelia A. Owens
*Attorney, Agent, or Firm*—Young & Thompson

[57] ABSTRACT

In the process for the hydroponic cultivation of aquatic plants and, in particular, water hyacinth, the plants are cultivated in a nutrient aqueous solution containing at least one nitrogen compound and elements such as P, K, Ca, Mg, S and Fe.

The nitrogen compound is formed by adding urea to the nutrient solution.

Use of the juice extracted from the resulting aquatic plant as a bio-stimulant for plant growth and seed germination.

3 Claims, 2 Drawing Sheets

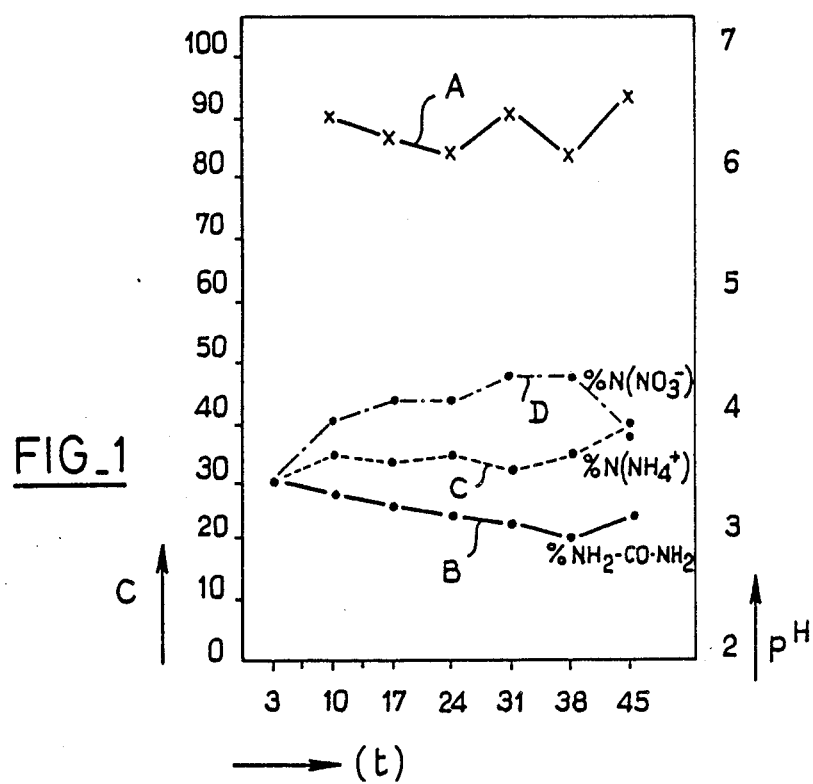
FIG_1
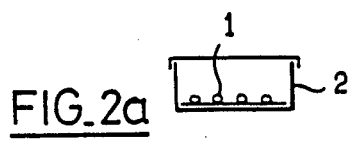
FIG_2a
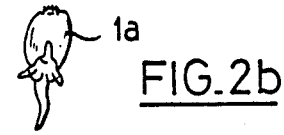
FIG_2b
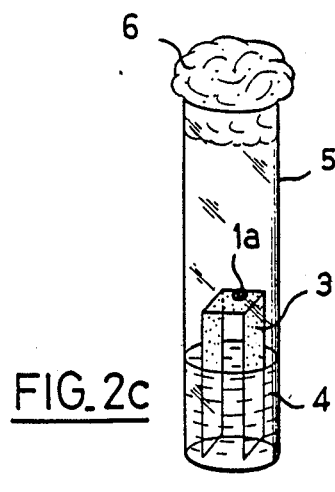
FIG_2c
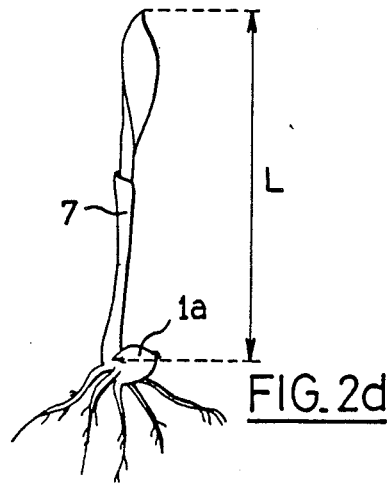
FIG_2d

PROCESS FOR THE CULTIVATION OF AQUATIC PLANTS, THE RESULTING PLANTS, AND THEIR USES

This application is a division, of application Ser. No. 908,817, filed Sept. 18, 1986 now abandoned.

BACKGROUND OF THE INVENTION

This invention relates to a process for the hydroponic cultivation of aquatic plants and, in particular, of the water hyacinth type (*Eichhornia crassipes*). The invention also relates to aquatic plants having the property of being adapted to cultivation similarly to water hyacinth, e.g. *lemna, spirodela, pistia*, etc. Aquatic plants of this type will hereinafter be referred to generally as water hyacinth.

The invention also relates to the aquatic plant and, in particular, the water hyacinth obtained by the said process, and the juice extracted from said water hyacinth, and its applications, inter alia as a plant growth biostimulant.

It is well known that water hyacinth is an aquatic plant whose growth is extremely rapid when the plant is in favourable ambient conditions.

DESCRIPTION OF THE PRIOR ART

Applicants have perfected a process and installation which are described in French patent application No. 2 559 639 of 17 Feb. 1984 in order that the cultivation of water hyacinth may be carried out under optimum conditions as regards plant yield.

It has been found that during its growth water hyacinth is capable of absorbing large quantities of nitrogen and mineral elements which may or may not be of use for its metabolism and which are contained in the water in which it is cultivated.

The absorbed nitrogen is converted more particularly into proteins. Thus depending on the nitrogen content of the water in which the water hyacinth grows, its protein content varies between 6 and 22% by weight of dry substance.

Some of the mineral elements absorbed by the water hyacinth are converted to chemical compounds, e.g. xanthophylls or carotenes, the content of which depends on the iron concentration of the water in which the water hyacinth grows. When the latter grows naturally, the xanthophyll content does not exceed 500 ppm and the carotene content does not exceed 20 ppm.

This property of water hyacinth, i.e. of fixing minerals in its tissues, has resulted in researchers using this plant to purify liquids containing undesirable mineral elements.

Other researchers have tried to increase the protein content of water hyacinth by adding a nitrogen compound to the water in which the plant is cultivated in order to form ammonium ions ($NH_4^+$) in said water, but although this known process gives a water hyacinth which has a higher protein concentration than that produced naturally, it has a very adverse effect on productivity.

SUMMARY OF THE INVENTION

One of the objects of this invention is to provide a process for the cultivation of aquatic plants and particularly water hyacinth whereby it is possible to obtain a plant very greatly enriched in nitrogen substance, more particularly in the form of proteins, with high productivity.

The invention therefore relates to a process in which the plants are cultivated in a nutrient aqueous solution containing at least one nitrogen compound and elements such as P, K, Ca, Mg, S and Fe, and in which the nitrogen compound is formed by adding urea.

Urea, whose chemical formula is $CO(NH_2)_2$ is decomposed under the action of the micro-organisms formed naturally in the nutrient aqueous solution as follows:

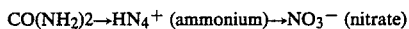

$$CO(NH_2)_2 \rightarrow HN_4^+ \text{ (ammonium)} \rightarrow NO_3^- \text{ (nitrate)}$$

Applicants have found that water hyacinth is capable of effectively absorbing the nitrogen in the above three forms, i.e. urea, ammonium and nitrate, and that in order to obtain a high rate of plant growth and high protein content thereof it is important that the above three forms are kept permanently present.

According to the invention, the process for the hydroponic cultivation of water hyacinth is characterised in that the supply of urea is adjusted so as to maintain a substantially stable equilibrium in the urea and its decomposition products under the action of the micro-organisms contained in the nutrient solution, i.e. $NH_4^+$ and $NO_3^-$, said nutrient agents being brought into contact with the hyacinth and more particularly its roots.

According to a preferred aspect of the invention, the supply of urea is so adjusted as to maintain substantially equal proportions in respect of urea and $NH_4^+$ and $NO_3^-$ ions with respect to the total nitrogen of the solution.

This gives the best rate of plant growth and the highest protein content.

The ambient conditions are also optimized by maintaining the pH of the nutrient solution at a value substantially between 5 and 7 and preferably at 6.5.

It has also been found experimentally that when the urea, $NH_4^+$ and $NO_3^-$ concentrations are equal, which presupposes that the rate of urea supply is equal to its rate of decomposition into $NH_4^+$ and $NO_3^-$, the pH of the nutrient solution is kept at a substantially constant value equal to 6.5, which is favourable. This fact can be explained as follows: the absorption of $NH_4^+$ by the plant results in acidification of the nutrient solution while the absorption of the $NO_3^-$ produces basification.

The nitrogen concentration in the above three forms in the nutrient solution is not very critical but is is preferable to keep this concentration at a value of between 100 and 1 000 ppm.

According to a specific aspect of the invention, the Fe content of the solution is adjusted to a value of between a few ppm and some tens of ppm so as to enrich the water hyacinth in respect of xanthophylls and carotenes.

The following is an example without any limiting force of the composition in gram-milliequivalents per liter of a nutrient solution used in the process according to the invention:

N ($NO_3^-$): 7.14
N ($NH_4^+$): 7,4
N $CO(NH_2)_2$: 7.4
P: 4.02
K: 3.97
Mg: 3.96
S($SO_4^-$): 2.61

Cl−: 2.25
Na+: 2.13
Ca−: 3.94
+ oligo-elements (traces).

DESCRIPTION OF THE DRAWINGS

In the accompanying drawings:
FIG. 1 is a graph in respect of the nutrient solution.
FIGS. 2a to 2d are diagrams showing the procedure used to test the bio-stimulant activity of the hyacinth juice.

DESCRIPTION OF THE PREFERRED EMBODIMENTS

Figure 3A:
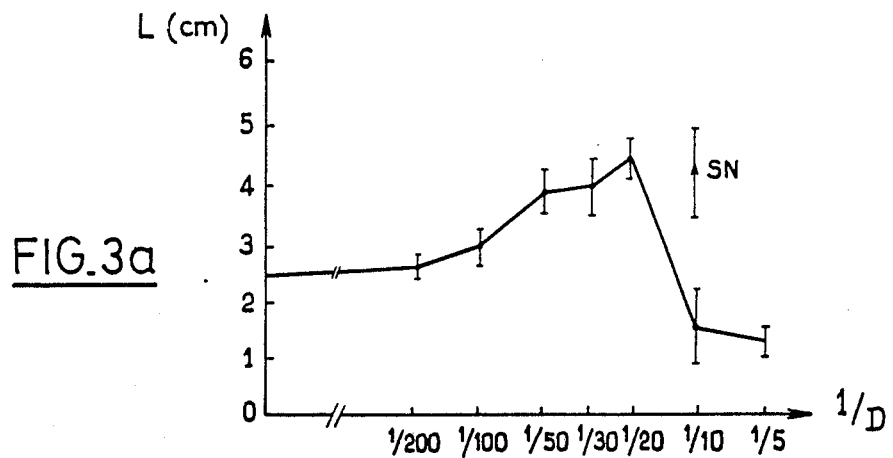
FIGS. 3a to 3c are the results of tests on the tomato.

FIG. 1 of the accompanying drawings is a graph showing the time t in days and the development of the pH of the nutrient solution (see curve A) and the distribution C in % of the nitrogen in the form of urea (curve B), $NH_4^+$ (curve C) and $NO_3^-$ (curve D).

In the example illustrated in this Figure, urea was added periodically practically every day to keep the nitrogen content of the solution at a substantially constant value of about 400 ppm.

FIG. 1 also shows that the pH remains substantially constant between 6 and 7 for the entire period of the test.

The process according to the invention gives a water hyacinth which unexpectedly has a very much greater protein content than the naturally cultivated plants, for the protein content of the latter is not more than 22% of dry substance when they grow naturally or by known processes.

Under the better conditions set forth hereinbefore, the water hyacinth obtained has a total nitrogen substance content, more particularly in protein form, of between 35 and 45% (expressed as percent of elementary nitrogen×6.25).

In view of the very significant difference in the protein contents of water hyacinth cultivated in accordance with the invention and the natural plants or those cultivated by known processes, it may be considered that the water hyacinth obtained by the specific hydroponic cultivation according to the invention, the constitution of the plant having been appreciably modified, constitutes a novel industrial product.

In addition, the water hyacinth productivity is 30 to 80 g in respect of dry substance per square meter of cultivated area and per day depending on the intensity of solar radiation.

The water hyacinth obtained in this way has a very high protein content and constitutes a both excellent and economic food inter alia for animals, and can advantageously replace other protein food such as soya.

If an iron compound which is soluble in the water of the nutrient solution, e.g. iron sulphate or iron in chelate form, is added, the invention gives a water hyacinth which additionally contains between 500 and 1 500 ppm of xanthophylls and between 20 and 500 ppm of carotenes.

The invention is therefore an economic way of effecting the synthesis of xanthophylls and carotenes of use in various applications of biochemistry or pharmacy.

One important and preferred application of the invention is the use of the juice produced by pressing at least some of the water hyacinth produced in accordance with the process of the invention, as a plant growth bio-stimulant and, in particular, as an accelerator for the rate of germination of seeds adapted to cultivation.

According to the invention it has surprisingly been found that this hyacinth juice has an effective action on the rate of plant growth and productivity, e.g. herbaceous plants, root and tuber plants, shrubs and flowers.

This juice contains nitrogen compounds, such as proteins, amino acids, peptides, vitamins, vegetable hormones, such as gibberelins, auxins and cytokinins, pigments such as xanthophylls and carotenes and mineral elements such as P, K, Ca, Mg, S, Cu, Zn, B, Mo, Mn.

Since the process according to the invention enables water hyacinth to be considerably enriched in nitrogen substance and since the juice extracted from this hyacinth as a high bio-stimulant action, this high nitrogen substance content combined with the presence of vitamins and mineral elements promotes the bio-stimulant action of the juice.

The hyacinth juice can be produced by pressing all the plant or just the leaves or roots and stems.

In use as a plant growth bio-stimulant it is preferable to use the root and stem juice because the leaves are an economic way of giving a protein concentrate which can be used directly in other applications such as foodstuff, more particularly for livestock.

Preferably, the juice is produced by crushing and pressing. After crushing and pressing of the plant the juice is filtered, if necessary by centrifugation in order to eliminate any solid particle in suspension and it is then immediately stabilized, e.g by the addition of a few percent of magnesium sulphate.

The juice obtained after filtration and before chemical stabilization contains between 1 and 2% by weight of dry substance, in the form of a mixture of the compounds listed hereinbefore.

The following is an example of the mineral composition of this juice:

| | |
|---|---|
| $Ca^{++}$ | 140 to 250 mg/l |
| $Mg^{++}$ | 70 to 150 mg/l |
| $K^+$ | 2 000 to 2500 mg/l |
| $Na^+$ | 150 to 200 mg/l |
| $Cl^-$ | 1 000 to 2600 mg/l |
| S (in the form of $SO_4^-$) | 200 to 500 mg/l |
| N (in the form of $NH_4^+$) | 200 to 400 mg/l |
| N (in the form of $NO_3^-$) | 100 to 200 mg/l |
| P | 400 to 500 mg/l |
| Fe | 1 to 5 mg/l |

This composition varies slightly depending on whether the juice is extracted from the enriched plant or just from the roots and stems or leaves.

Of course this composition also varies depending upon the nitrogen substance and mineral element composition of the nutrient solution used for the cultivation of the water hyacinth.

For the purposes of storage and transportation of the hyacinth juice the invention proposes that the juice should be stabilized in that form by the addition of a salt (for example magnesium sulphate) or that the juice should previously be concentrated by evaporation without changing the product (at atmospheric pressure or in a partial vacuum). The juice can be concentrated about 20 times, i.e. 5 liters to 100 liters of initial juice. The concentrated juice is easier to store, the mineral compounds present in the juice providing stabilization which allows long storage.

For use as a plant growth stimulator, a water hyacinth juice which has not previously been concentrated and which initially contains 1 to 2% of dry substance is diluted at the rate of 5 to 30 liters of water/liters of juice.

This stabilized and diluted juice is sprayed on cultivated plants in a proportion of 300 to 1500 liters per hectare of crop.

The following are two examples of experimentation on plant cultivation by the spraying of hyacinth juice. These experiments were carried out under Professor Pierre GRIGNAC (Chair of Phytotechnology at the Ecole Nationale Superieure Agronomique of Montpellier), and show the growth stimulating role of the juice applied by foliar spraying.

The juice used in these examples was obtained by crushing and pressing roots and stems of water hyacinth cultivated in an installation in accordance with that described in French patent application No. 2 559 639 of 17 Feb. 1984 in applicants' name. The nutrient solution in this installation was given daily additions of nitrogen in the form of urea in accordance with the process according to the invention.

EXAMPLE 1

Experimentation with juice on potatoes (Test carried out in a closed forbidden-access field)

Crop characteristics:

Variety Claustar, minimum size seed, class A, origin Brittany, pregerminated seed.

Previous crop: peas followed by winter lettuce destroyed by the cold in January and buried by the mud.

Preparation of soil: tilling followed by rotary harrow

Manuring: 150 kg $P_2O_5$, $K_2O$ on tilling 150 kg $N=100$ on planting, 50 on first harrowing Plant: 2nd March, spacing: 65 cm–30 cm Lifting: 25–30 March: harrowing 15 April –10 May Irrigation by water: 8 May, 22 May, 11 June, amount supplied 180 mm.

The potatoes were sprayed with hyacinth juice according to the invention with a 5 times water dilution.

One batch A of potatoes was sprayed with 500 l of dilute juice per hectare.

One batch B of potatoes was sprayed with 1 000 l of dilute juice per hectare.

One batch C of potatoes was sprayed with 1 500 l of dilute juice per hectare.

One batch T (control) was sprayed with 1 000 l of pure water (without hyacinth juice).

Two sprayings were carried out each containing half the dose, i.e.:

On 20 April: at the 4–5 leaf stage

On 13 May: at the beginning of the show of flower buds.

RESULTS: Crop of 30 May

Yield (in tonnes per hectare)

| | Total (T/ha) | Commercial* | Tailings (<40 mm) | Number of tubers per plant (>40 mm) |
|---|---|---|---|---|
| T | 28.8 a | 20.5 a | 8.3 a | 4.8 a |
| A | 31.8 b | 24.2 b | 7.6 a | 4.9 a |
| B | 34.5 c | 28.3 c | 6.2 b | 5.3 a |
| C | 34.8 c | 29.8 c | 5.0 c | 5.5 a |

*"Commercial" means marketable potatoes.

The letter a denotes a result which is not significantly different from the control treatment T.

The letter b denotes an improved result as compared with the control treatment.

The letter c denotes a very much improved result as compared with the control treatment.

These results show that the spraying of hyacinth juice improves the increase in size of potato tubers.

Crop of 16 June

Yield (in tonnes per hectare)

| | Total (T/ha) | Commercial | Tailings (<40 mm) | Number of tubers per plant (>40 mm) |
|---|---|---|---|---|
| T | 32.4 a | 28.0 a | 4.4 | 5.2 a |
| A | 34.8 b | 31.4 b | 3.4 a | 5.8 a |
| B | 37.4 c | 34.2 c | 3.2 a | 6.0 a |
| C | 37.5 c | 34.3 c | 3.2 a | 6.1 a |

This result shows that the number of tubers was not affected by the treatment according to the invention and this takes effect in the form of a better migration of reserves and hence larger tubers.

Crop of 1st July

| | Total (T/ha) | Commercial | Tailings (<40 mm) | Number of tubers per plant (>40 mm) |
|---|---|---|---|---|
| T | 38.5 a | 35.5 a | 3.0 a | 5.4 a |
| A | 41.6 b | 38.7 b | 2.9 a | 6.0 b |
| B | 44.9 c | 42.5 c | 2.4 a | 6.3 b |
| C | 45.2 c | 42.7 c | 2.5 a | 6.4 b |

This result shows that on maturity there is also an improvement in yield due largely to an increase in the individual weights of the tubers.

Analyses: dry substance content

| | Crop of 30 May | Crop of 16 June | Crop of 1st July |
|---|---|---|---|
| T | 18.5 | 22.0 | 24.5 |
| A | 18.0 | 22.0 | 24.5 |
| B | 17.5 | 21.5 | 24.0 |
| C | 17.5 | 21.0 | 24.0 | content of glucides (g) and proteins (p)

| | Crop of 30 May | | Crop of 16 June | | Crop of 1st July | |
|---|---|---|---|---|---|---|
| | g | p | g | p | g | p |
| T | 14.0 | 3.5 | 17.5 | 3.2 | 19.0 | 3.2 |
| A | 13.5 | 3.5 | 17.5 | 3.1 | 19.1 | 3.2 |
| B | 13.5 | 3.5 | 17.0 | 3.0 | 19.1 | 3.3 |
| C | 13.5 | 3.8 | 17.0 | 3.1 | 19.1 | 3.3 |

The treatment according to the invention does not therefore affect the composition of the tubers.

There was some delay in the vegetation resulting in a slightly greater water content in the first two crops.

It was also found that the number of stem branchings was greater and the height of the stems and of the foliar surface are increased.

In conclusion, two sprayings with dilute water hyacinth juice considerably improve the crop yield of early or full season vegetables.

EXAMPLE 2

Experiment with juice on beetroot

Crop characteristics:

Variety: improved Egyptian plate: polygerm Previous crop: green beans harvested in September Preparation: chisel followed by rotary harrow Manuring: 150 kg $P_2O_5$, 180 kg $K_2O$ chisel 200 kg/N: 100 kg lifting, 100 kg at the 5-6 leaf stage Sowing: 14 February under plastic film Lifting: 5 March Uncovered: 3 April a little late: 4-5 leaf stage Crop density: 1 plant every 10 cm Line spacing: 25 cm (high crop density) Harrowing: 3 April, 30 April, 18 May Irrigation: 8 May, 22 May, 11 June: amount supplied 180 mm Experimental treatments:

Spraying with a 5 x diluted hyacinth juice:

A = 500 l/ha

B = 1 000 l/ha

T = 1 000 l/ha pure water In two applications: 5 April: at the 5-6 leaf stage 30 April: at the start of root enlargement. Crops staggered from 20 May: harvesting of 1 linear meter once per week.

RESULTS

Weight of marketable roots

| Date | Yield in kg per m² | | |
|---|---|---|---|
| | T | A | B |
| 20/5 | 1.5 a | 1.8 b | 1.9 b |
| 28/5 | 1.8 a | 1.9 a | 2.0 a |
| 5/6 | 2.0 a | 2.4 b | 2.6 b |
| 13/6 | 2.4 a | 2.7 b | 2.8 b |
| 20/6 | 2.5 a | 2.8 b | 3.1 c |
| 28/6 | 2.9 a | 3.2 b | 3.5 c |
| 3/7 | 3.1 a | 3.6 b | 3.9 c |

The letters a, b, c have the same meanings as in Example 1.

The above results therefore show that the hyacinth juice according to the invention significantly promotes beetroot growth.

Other experiments with foliar spraying carried out by applicants show that the hyacinth juice also has a favourable effect on the growth of plants such as herbaceous plants, root and tuber plants, shrubs and flowers.

Apart from the plant growth stimulation by foliar spraying, applicants have found that water hyacinth juice from the whole plant or parts thereof, either in their natural form or concentrated, and stabilized, have a stimulant effect on seed germination.

For example, in vitro tests were carried out on tomato and corn seeds. This test method is shown in FIGS. 2a, b, c. The seeds were germinated (FIG. 2a) in a Petri dish 2 for 48 hours at 24° C. in darkness. The seeds 1a having germinated (FIG. 2b) were placed on a filter paper 3 bent as shown in the drawing, dipping into a water hyacinth juice 4 contained in a test tube 5 closed by cotton 6 (FIG. 2c). This tube was kept at 24° C. for a week in a 70% relative humidity with artificial lighting 16 hours per day.

The measurements related to the speed of germination of the seed 1 and the length L of the seedling 7 (FIG. 2d).

The following five types of juice obtained by cold pressing were tested by way of example:

| | |
|---|---|
| Juice No. I | Whole plant |
| Juice No. II | Uncrushed green part |
| Juice No. III | Uncrushed white part (roots and stems) |
| Juice No. IV | Crushed white part (roots and stems) |
| Juice No. V | Crushed green part |

These juices were clarified by centrifugation.

Experiments show that all the juices prepared in this way have bio-stimulant action but that this could vary in intensity depending on the nature of the plant.

Figure 3B:
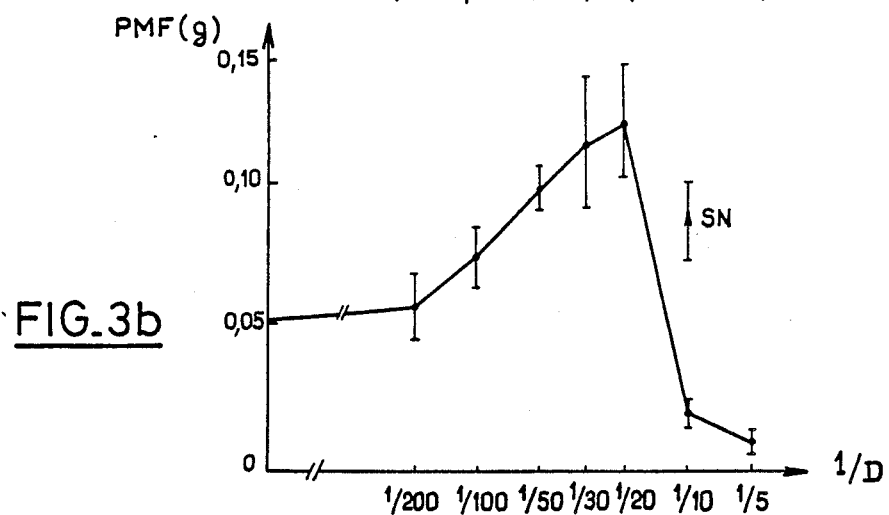
Figure 3C:
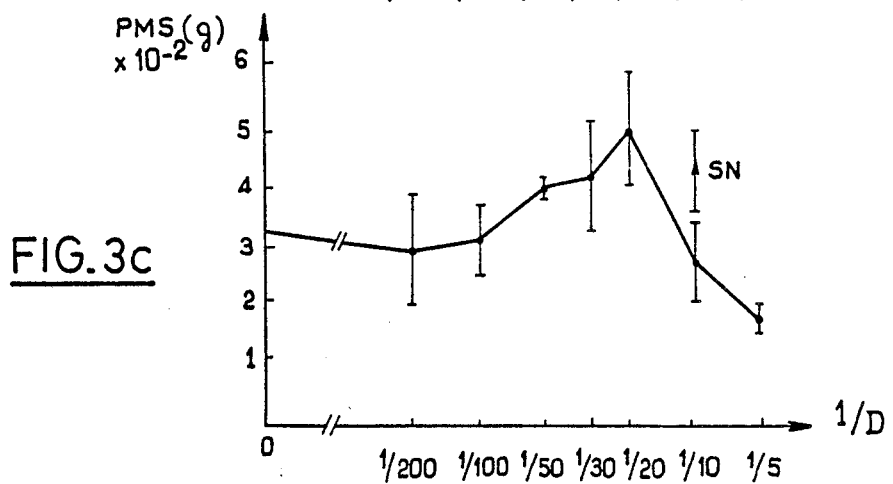

For example, FIGS. 3a, 3b and 3c of the accompanying drawings are examples of the effect of juice No. IV on the tomato. In these Figures, the reciprocals 1/D of the dilution ratio D are shown on the x-axis while the y-axis shows the following:

Average length of stem L (FIG. 3a)

Average weight of fresh matter PMF (stems and roots) of young plants (FIG. 3b)

Average weight of dry substance PMS of young plants (FIG. 3c)

Each point indicated is the average ±typical deviation of 15 to 20 observations. SN denotes the results obtained by dipping the filter paper into a control nutrient solution.

In this example, irrespective of the criterion, it appears that juice No. IV with a 20× dilution has maximum activity. Lower concentrations are less active or inactive. Higher concentrations become inhibitive.

With regard to juices I, II and III, the slope of the curves obtained in respect of the tomato seedlings remains the same. The maximum stimulant effect is abut 80% for the 10× diluted juice. Juice No. V has a stimulating effect up to the maximum concentration tested (juice with a 5× dilution).

This germination activating effect produced by the juice of water hyacinth cultivated in this way, the juice having been brought into contact with the seed, is particularly advantageous and the characteristics of the adult plant are not changed.

Of course the invention is not limited to the examples that have been described and numerous modifications can be made thereto without departing from the scope of the invention.

Moreover, other aquatic plants have the ability to absorb mineral elements and particularly nitrogen introduced in aqueous nutrient solution and are capable, like water hyacinth, of converting this nitrogen into protein, amino acids, peptides, etc.

These plants are more particularly lemna, spirodela, pistia, etc.

The invention therefore also covers these aquatic plants.

I claim:

1. A method for the bio-stimulation of the growth of plants, said method comprising applying to plants under cultivation an effective bio-stimulating amount of a bio-stimulant solution derived from water hyacinth, said solution produced by the steps of pressing the water hyacinth to obtain a juice, and filtering the resulting juice to obtain said solution comprising from between 1 and 2 percent solids by weight, said bio-stimulant solution being applied to said plants in diluted form, said dilution being in the proportion of 5 to 30 liters of water to 1 liter of solution and said diluted solution being sprayed on the cultivated plants in a proportion of 300 to 1500 liters per hectare.

2. The method of claim 1 wherein said juice is derived from water hyacinth by pressing the roots and stems of the water hyacinth.

3. The method of claim 1 wherein said plants are selected from the group consisting of herbaceous plants, root and tuber plants.

* * * * *